United States Patent [19]
Castillo

[11] Patent Number: 5,571,073
[45] Date of Patent: Nov. 5, 1996

[54] CATHETER FLEXIBLE TIP ASSEMBLY

[75] Inventor: Frank O. Castillo, Miami Lakes, Fla.

[73] Assignee: Cordis Corporation, Miami Lakes, Fla.

[21] Appl. No.: 548,781

[22] Filed: Oct. 26, 1995

Related U.S. Application Data

[63] Continuation of Ser. No. 187,836, Jan. 28, 1994, abandoned.

[51] Int. Cl.$^6$ ................................................. A61M 25/00
[52] U.S. Cl. ........................ 604/282; 604/280; 128/658; 138/133
[58] Field of Search .................................. 604/280–283, 604/96, 264; 128/657, 658, 772; 138/123, 127, 129, 133

[56] References Cited

U.S. PATENT DOCUMENTS

| | | |
|---|---|---|
| 3,426,744 | 2/1969 | Ball . |
| 3,618,613 | 11/1971 | Schulte . |
| 3,890,976 | 6/1975 | Bazell ..................... 128/351 |
| 4,044,765 | 8/1977 | Kline . |
| 4,531,943 | 7/1985 | VanTassel ................ 604/280 |
| 4,665,604 | 5/1987 | Dubowik . |
| 4,705,511 | 11/1987 | Kocak . |
| 4,737,153 | 4/1988 | Shimamura ............. 604/282 |
| 4,886,506 | 12/1989 | Lougren .................. 604/282 |
| 4,899,787 | 1/1990 | Ouchi ..................... 604/282 |
| 4,955,862 | 9/1990 | Sepetka . |
| 5,069,674 | 12/1991 | Fearnot ................... 604/282 |
| 5,112,304 | 5/1992 | Barlow et al. . |
| 5,178,158 | 1/1993 | de Toledo ............... 604/282 |
| 5,254,107 | 10/1993 | Soltesz .................... 604/282 |
| 5,279,596 | 1/1994 | Castaneda et al. ...... 604/282 |
| 5,290,230 | 3/1994 | Ainsworth et al. . |
| 5,314,418 | 5/1994 | Takano ................... 604/282 |
| 5,318,032 | 6/1994 | Lonsbury ................ 128/658 |
| 5,334,169 | 8/1994 | Brown et al. . |
| 5,403,292 | 4/1995 | Ju ........................... 604/282 |

OTHER PUBLICATIONS

Polyurethanes: The Bridge Between Silicone Rubbers and Plastics (Durometer Conversion Chart).
Roff, *The Handbook of Common Polymers*, Section 40: Polyurethanes., 1971, pp. 446 and 455.

*Primary Examiner*—Randall L. Green
*Assistant Examiner*—Chalin Smith
*Attorney, Agent, or Firm*—Thomas R. Vigil

[57] ABSTRACT

The catheter flexible tip assembly is mounted to the distal end of a catheter body having high torque and kink resistant characteristics. The tip assembly comprises a distal end portion including a soft tubular body having a wire coil embedded therein and a transitional tip portion connected between the proximal end of the distal end portion and the distal end of the catheter body. Preferably a high stress resistant connection is provided between a distal end of the transitional tip portion and a proximal end of the distal end portion. The connection is defined by a proximal end portion of the wire coil in the distal end portion extending beyond the proximal end of the distal end portion and being received in an enlarged bore which is located at the distal end of the transitional tip portion and which is coaxial with a lumen of the catheter body and fused to the wall of the bore and by the distal end of the transitional tip portion being heat butt fused to a proximal end of the soft tubular body of the distal end portion. In another embodiment the tip assembly comprises the distal end portion and a high stress resistant connection between a distal end of the catheter body and a proximal end of the distal end portion. The connection is defined by the distal end of the catheter body being conical and being received in and heat fused to the wall of a conical cavity in the proximal end of the distal end portion.

36 Claims, 2 Drawing Sheets

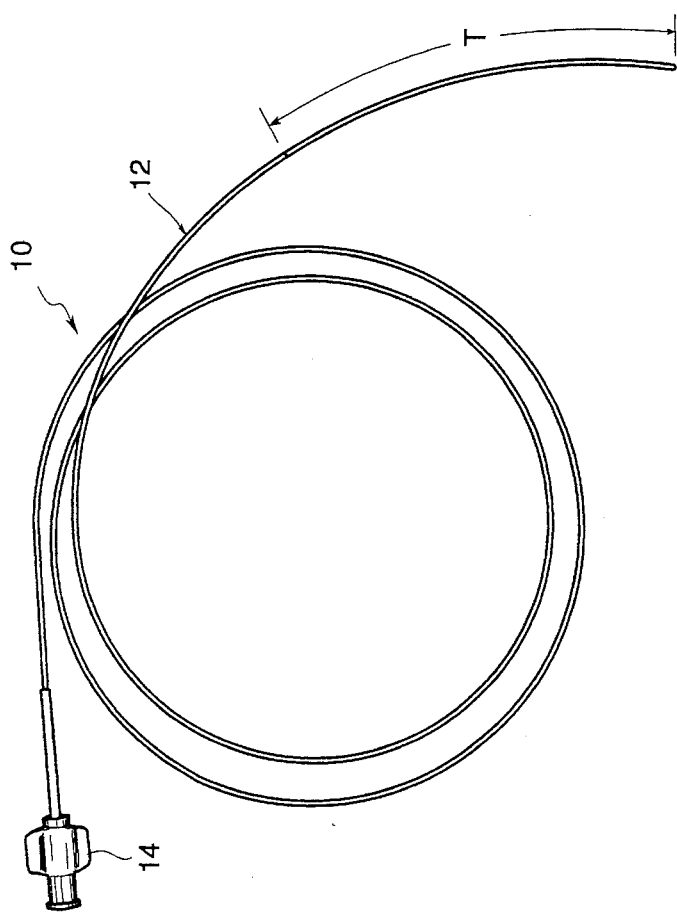
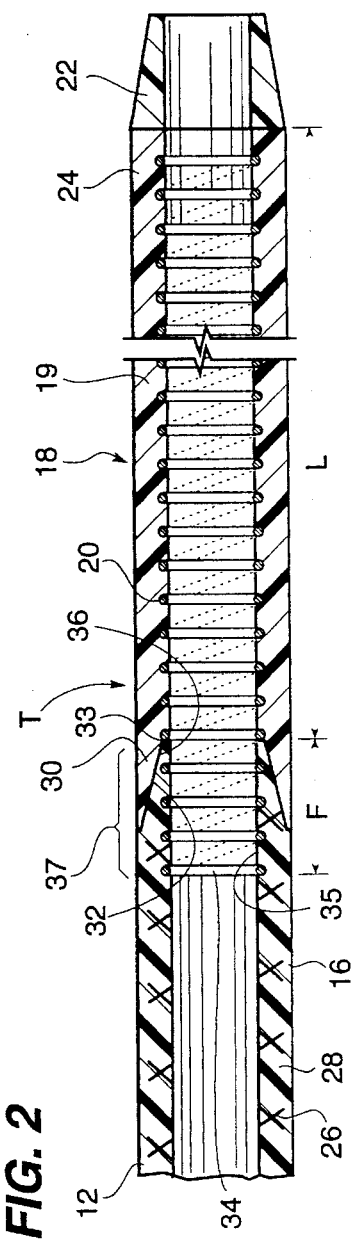
FIG. 1
FIG. 2

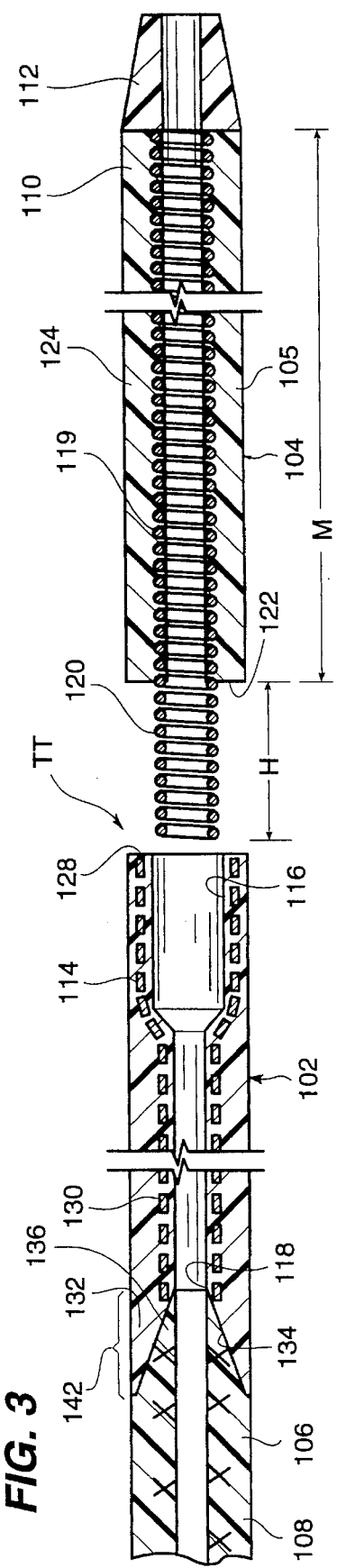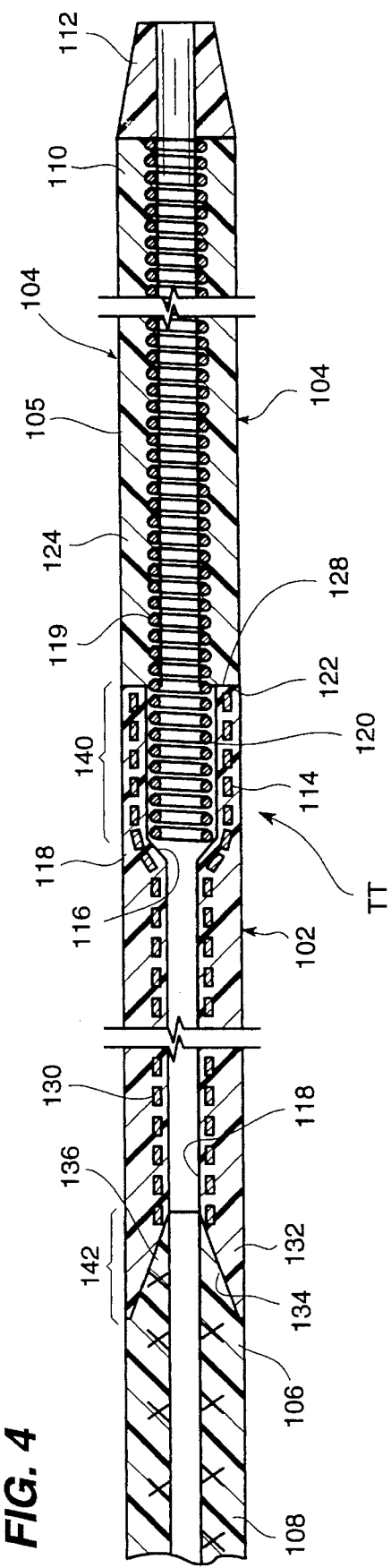

CATHETER FLEXIBLE TIP ASSEMBLY

BACKGROUND OF THE INVENTION

Cross Reference to Related Application

This is a continuation of application Ser. No. 08/187,836 filed Jan. 28, 1994 now abandoned.

1. Field of the Invention

The present invention relates to a catheter flexible tip assembly fused to the distal end of a high torque/kink resistant catheter body. The flexible tip assembly includes an overlap fused area between a proximal end of a distal end (tip) portion of the assembly and the distal end of the catheter body. The distal end portion is made of a soft flexible material with a stainless steel coil embedded therein with a portion of the coil extending proximally from the distal end portion for insertion into a lumen of the assembly and for embedding into the walls of the lumen.

2. Description of the related art including information disclosed under 37 CFR §§1.97–1.99.

Heretofore, various kink resistant intravascular catheters and catheters with a coiled wire embedded therein have been proposed. Examples of several previously proposed catheters are disclosed in the following U.S. Patents:

| U.S. Pat. No. | Patentee |
| --- | --- |
| 3,426,744 | Ball |
| 3,618,613 | Schulte |
| 4,044,765 | Kline |
| 4,665,604 | Dubowik |
| 4,705,511 | Kocak |
| 5,112,304 | Barlow et al. |

The Ball U.S. Pat. No. 3,426,744 discloses a heart pump cannula in which a proximal portion of the cannula is made of an elastic material that is reinforced with a helical tubular sleeve of a material such as rayon or nylon cord. The distal portion of this cannula is a balloon, as particularly shown in FIG. 2. This differs significantly from the disclosure of this invention in which the proximal portion thereof is of greater torsional stiffness than the distal portion and is preferably reinforced with a braided wire tubular support member, while the distal portion of this invention constitutes a typically short segment of plastic tubing reinforced with a helical wire.

The Schulte U.S. Pat. No. 3,618,613 discloses a catheter having a wire spring coiled around the catheter tubing in interference fit and then coated with a silicone material to provide the surface finish required for insertion. Applicants' attorney does not see any teaching of a proximal portion having greater torsional stiffness than the distal portion, which distal portion has greater bendability than the proximal portion.

The Kline U.S. Pat. No. 1 4,044,765 discloses a flexible tube for intravenous feeding comprising a body formed from a continuously wound coil spring in which the helices thereof are in mutual contact and in which the spring is at least externally sheathed with a smooth, inert, impervious transparent plastic material firmly bonded thereto.

The Dubowik U.S. Pat. No. 4,665,604 discloses a non-fused catheter having a stiff braid-reinforced body and a pliable non-braided tip.

The Kocak U.S. Pat. No. 4,705,511 shows an introducer sheath assembly which comprises a flexible tube for intravenous use at the outlet, including a helical coiled spring having a plurality of coils, which spring is surrounded by a thin, cylindrical wall, apparently along the entire length thereof.

The Barlow et al. U.S. Pat. No. 5,112,304 discloses a balloon catheter having a inner tube of elastomeric material containing a guidewire passage and having a spring embedded therein.

Also an intravascular catheter with a kink resistant tip including a soft tip portion with a stainless steel coil therein which is butt fused (thermal welded) to a high torque/kink resistant proximal catheter portion is disclosed in U.S. Pat. No. 5,279,596 the disclosure of which is incorporated herein.

SUMMARY OF THE INVENTION

According to the present invention there is provided a catheter flexible tip assembly mounted to the distal end of a catheter body having high torque and kink resistant characteristics. The tip assembly comprises a distal end portion including a soft tubular body having a wire coil embedded therein and a high stress resistant connection between a distal end of the catheter body and a proximal end of the distal end portion. The connection is defined by the distal end of the catheter body being conical and being received in and heat fused to the wall of a conical cavity in the proximal end of the distal end portion.

Also according to the present invention there is provided a catheter flexible tip assembly mounted to the distal end of a catheter body having high torque and kink resistant characteristics. The tip assembly comprises a distal end portion including a soft tubular body having a wire coil embedded therein and a high stress resistant connection between a distal end of the catheter body and a proximal end of the distal end portion. The connection is defined by a proximal end portion of the wire coil extending beyond the proximal end of the distal end portion and being received in an enlarged bore which is located at the distal end of the catheter body and which is coaxial with a lumen of the catheter body and being fused to the wall of the bore and by the distal end of the catheter body being heat butt fused to a proximal end of the soft tubular body of the distal end portion.

Further according to the present invention there is provided a catheter flexible tip assembly mounted to the distal end of a catheter body having high torque and kink resistant characteristics. The tip assembly comprises a distal end portion including a soft tubular body having a wire coil embedded therein and a transitional tip portion connected between the proximal end of the distal end portion and the distal end of the catheter body.

BRIEF DESCRIPTION OF THE DRAWINGS

FIG. 1 is a plan view of a coiled intravascular catheter constructed in accordance with the teachings of the present invention;

FIG. 2 is an enlarged longitudinal sectional view through an end portion of the catheter shown in FIG. 1 and shows the connection between a high torque/kink resistant proximal catheter portion and a soft flexible catheter tip assembly having a stainless steel coil therein and constructed in accordance with the teachings of the present invention;

FIG. 3 is a longitudinal view, partially in section, of another embodiment of the catheter tip assembly of the present invention which includes a transition tip portion which is positioned between the super torque body and a flexible distal (tip) end portion and shows the flexible distal end portion separated from the transition tip portion; and, FIG. 4 is a longitudinal view, partially in section, of the catheter tip assembly shown in FIG. 3 but with the transition tip portion connected to the distal end portion. The tip assembly comprises a distal end portion including a soft tubular body having a wire coil embedded therein and a transitional tip portion connected between the proximal end of the distal end portion and said catheter body.

DESCRIPTION OF THE PREFERRED EMBODIMENT(S)

Referring now to FIG. 1 in greater detail, there is illustrated therein an intravascular catheter 10, including a catheter body 12 extending from a connector 14 at the proximal end of the catheter, to a flexible tip assembly T constructed according to the teachings of the present invention.

As best shown in FIG. 2, the flexible tip assembly T includes a distal end 16 of the catheter body 12 which is connected/fused to a soft flexible tip or distal end portion 18 including a soft tubular body 19 having a stainless steel coil spring 20 embedded therein and a soft plug tip 22 fused to a distal end 24 of the distal end portion 18.

The catheter body 12 is of the type which includes cross-braided reinforcement 26 embedded within a tubular body 28 and can be of the type disclosed in U.S. Pat. No. 4,665,604 or U.S. Pat. No. 5,279,596 the disclosure of which is incorporated herein by reference.

The body 19 of the flexible distal end (tip) portion 18 is preferably made of an 80 A plastic material sold under the trademark PELLETHANE and commonly known as P/N 2939651. The length L of the tip portion 18 is between 10 and 20 centimeters and preferably between 12 to 15 centimeters and the coil spring 20 has an outer diameter of approximately 0.0405 inches.

According to the teachings of the present invention, a proximal end 30 of the distal end portion 18 has a conical cavity 32 extending from the outer diameter of the tip portion 18 to a coil 33 of the coil spring 20 from which a proximal end 34 of the coiled spring 20 extends into a lumen 35 in the distal end 16 of the catheter body 12 a distance F which is preferably 2 centimeters±5 millimeters.

As shown, the distal end 16 of the catheter body 12 has an outer conical end 36 having the same taper as the inner conical cavity 32 at the proximal end 30 of the distal end portion 18.

It will be understood that when the proximal end 30 of the distal end portion 18 with the coil spring proximal end portion 34 extending proximally therefrom is inserted into the lumen 35 of, and the cavity 32 over the distal tapered end 36 of, the catheter body 12 and heat fused to the proximal end 30 of the catheter body 12, a highly stress resistant joint or connection 37 is created. This is established by the overlapping and mating tapered ends (conical end 36 in conical cavity 32), by the length of the taper, approximately 1.5 centimeters, and by the length of, (2 cm), and the embedding of, the proximal end portion 34 of the coil spring 20 in the wall of the lumen 35. This joint or connection 37 provides the tip assembly T with a very special flexible and pushable quality whereby a physician is provided with a flexible catheter tip which he can maneuver very easily in very difficult situations because the coil spring 18 and the 80 A PELLETHANE distal (tip) end portion combined together provide a desired quality of strength, softness and variable control required in negotiating blood vessels with very tortuous shapes, such as those found in the brain area.

The length of the stainless steel wire coil spring 20 is F plus L, typically 14 centimeters.

The soft tip plug 22 can be made of several different materials and is typically made of 55 D a plastic material sold under the trademark PELLETHANE.

Referring now to FIGS. 3 and 4, there is illustrated therein a flexible catheter tip assembly TT which includes a transitional tip portion 102 interposed between a distal (tip) end portion 104, including a soft tubular body 105, and a distal end 106 of a catheter body 108. Fused to a distal end 110 of the distal end portion 104 is a soft tip plug 112 which can be made of 55 D plastic material sold under the trademark PELLETHANE.

As shown in FIG. 3, a distal end 114 of the transitional tip portion 102 has an enlarged bore 116 formed therein, which is typically formed with a straight round end mandrel (not shown) so that the bore 116 is larger than the lumen 118 of the transitional tip portion 102.

The body 105 of the distal end portion 104 has a stainless steel coil spring 119 (similar to coil spring 20 in FIG. 2) embedded therein with a proximal end portion 120 extending a distance H from a proximal end 122 of the soft tip body 124 of the distal end portion 104. The distance H is typically 2 cm.±5 mm. It will be understood that the depth of the enlarged bore 116 is approximately the same length H as the proximal end 120 of the coil spring 119. The coil spring proximal end portion 120 is received in the bore 116 and fused therein by heat welding and at the same time the proximal end 122 of the distal end portion 104 is butt fused to a distal end 128 of the transitional tip portion 102.

According to the teachings of the present invention, the transitional tip portion 102 has a flat stainless steel coil spring 130 embedded therein adjacent the lumen 118 and can have a length of 3–5 cm. between the distal end portion 106 and the catheter body 108. The transitional tip portion is preferably made of 55 D plastic material sold under the trademark PELLETHANE.

In a manner similar to that described in connection with the description of FIG. 2, a proximal end 132 of the transitional tip portion 102 has a conical or tapered cavity 134 extending outwardly from the lumen 118 for receiving therein and being fused to a conical distal end 136 of the catheter body 108 which is constructed in the same manner as the catheter body 28 shown in FIG. 2.

The fused together components of the catheter flexible tip assembly TT is illustrated in FIG. 4. The distal end portion 104 is preferably made of 80 A plastic material sold under the trademark PELLETHANE and has a length M of 10–20 cm., preferably 12–15 cm. The outer diameter of the distal end portion is typically approximately 0.066 inches. Also, while the coiled spring 130 is preferably flat, it can also be round. Further, the catheter body can be made of a cross braided reinforcement wires embedded in a tubular body which is sold under the trademark DUCOR, as is well known in the art.

It will be appreciated that the catheter tip assembly TT shown in FIGS. 3 and 4 has the advantage of providing a an intermediate transitional tip portion 102 between the catheter body 108 and the distal (tip) end portion 104 which is softer than catheter body 108 but not as soft as the distal end portion 104 to facilitate bending and flexing of the tip assembly TT when it is inserted into a blood vessel which has a tortuous path, such as blood vessels in the brain. At the same time, high stress resistant joints or connections 140 (between the distal end portion 104 and the transitional tip portion 102) and 142 (between the transitional tip portion 104 and the catheter body 108) are provided.

From the foregoing description, it will be apparent that the catheter tip assembly T or TT of the present invention has a number of advantages, some of which have been described above and others of which are inherent in the invention. Also it will be understood that modifications can be made to the catheter tip assembly T or TT described above without departing from the teachings of the present invention. Accordingly, the scope of the invention is only to be limited as necessitated by the accompanying claims.

We claim:

1. A catheter flexible tip assembly combined with and mounted to the distal end of a catheter body, said catheter body having high torque and high kind resistant characteristics, having a central lumen and having a distal end with a conical outer surface, said tip assembly comprising an elongate soft body having a wire coil embedded therein, a distal end having a tip plug and a proximal end, and a high stress resistant connection between said distal end of said catheter body and said proximal end of said elongate soft body of said tip assembly, said high stress resistant connection being defined a conical cavity in said proximal end of said elongate soft body, by said conical distal end of said catheter body being received in and heat fused to a wall of said conical cavity in said proximal end of said elongate soft body and by said wire coil in said elongate soft body having a proximal end which extends proximally beyond said proximal end of said elongate soft body and into said conical cavity and beyond the outer end of said conical cavity and is embedded in and heat fused into a wall of a distal portion of said central lumen in said catheter body.

2. The catheter tip assembly of claim 1 wherein high stress resistant connection is further defined by said conical distal end of said catheter body having a length of substantially 1.5 cm.

3. The catheter tip assembly of claim 2 wherein said proximal end of said wire coil has a length of substantially 2 cm.±5 mm.

4. The catheter tip assembly of claim 1 wherein said elongate soft body is made of a plastic material having a shore "A" durometer of substantially 80 A.

5. The catheter tip assembly of claim 1 wherein said catheter body is made of a material having cross-braided reinforcement members therein.

6. The catheter tip assembly of claim 1 wherein said elongate soft body has a length of between 10–20 cm.

7. The catheter tip assembly of claim 1 wherein said elongate soft body has an outer diameter of substantially 0.066 inches.

8. The catheter tip assembly of claim 1 including a tip plug fixed to the outer end of said elongate soft body.

9. The catheter tip assembly of claim 1 wherein said tip plug is made of a plastic material having shore a "D" durometer of substantially 55.

10. The catheter tip assembly of claim 1 wherein said elongate soft tubular body has a length of between 12–15 cm.

11. A catheter flexible tip assembly combined with and mounted to the distal end of a catheter body portion, said catheter body portion having a central lumen therein, having wire reinforcement therein and having high torque and high kink resistant characteristics, said tip assembly comprising an elongate soft body having a wire coil embedded therein, a proximal end and a distal end with a tip plug, and a high stress resistant connection between a distal end of said catheter body portion and a proximal end of said elongate soft body, said high stress resistant connection being defined by said distal end of said catheter body portion having an enlarged bore therein with a cross-section larger than the cross-section of said central lumen, by a proximal end portion of said wire coil extending beyond the proximal end of said elongate soft body and being received in said enlarged bore and heat fused to the wall of said bore and by the distal end of said catheter body being heat butt fused to said proximal end of said elongate soft body.

12. The catheter tip assembly of claim 11 wherein said proximal end of said wire coil has a length of substantially 2 cm.±5 mm.

13. The catheter tip assembly of claim 10 wherein said elongate soft body is made of a plastic material having a shore "A" durometer of substantially 80 A.

14. The catheter tip assembly of claim 11 wherein said catheter body is made of a material having cross-braided reinforcement members therein.

15. The catheter tip assembly of claim 11 wherein said elongate soft body has a length of between 10–20 cm.

16. The catheter tip assembly of claim 11 wherein said elongate soft body has an outer diameter of substantially 0.066 inches.

17. The catheter tip assembly of claim 11 including a tip plug fixed to the outer end of said elongate soft body.

18. The catheter tip assembly of claim 11 wherein said tip plug is made of a plastic material having shore "D" durometer of substantially 55.

19. The catheter tip assembly of claim 11 wherein said elongate soft tubular body has a length of between 12–15 cm.

20. A catheter flexible tip assembly combined with and mounted to a distal end of a catheter body, said catheter body having high torque and high kink resistant characteristics, having a central lumen and having a distal end with a conical outer surface, said tip assembly comprising an elongate soft tubular body having a wire coil embedded therein, a distal end having a tip plug and a proximal end, a transitional tip portion connected between said proximal end of said elongate soft tubular body and the distal end of said catheter body, a first high stress resistant connection between said distal end of said catheter body and a proximal end of said transitional tip portion defined by a conical cavity in said proximal end of said transitional tip portion, and by said conical distal end of said catheter body being received in and heat fused to a wall of said conical cavity in said proximal end of said transitional tip portion and a second high stress resistant connection between a distal end of said transitional resistant connection between a distal end of said transitional tip portion and said proximal end of said elongate soft tubular body defined by said distal end of said transitional tip portion having an enlarged bore therein with a cross-section larger than the cross-section of said central lumen, by a proximal end portion of said wire coil extending beyond said proximal end of said elongate tubular body and being received in said enlarged bore and heat fused to the wall of said bore and by the distal end of said transitional tip portion being heat butt fused to a proximal end of said elongate soft tubular body.

21. The catheter tip assembly of claim 20 wherein said transitional tip portion has a length of between approximately 2 and 5 cm.

22. The catheter tip assembly of claim 20 wherein said transitional tip portion comprises a soft tubular body having a coil spring embedded therein.

23. The catheter tip assembly of claim 20 wherein said wire coil in said transitional tip portion is a flat wire coiled into a spring.

24. The catheter tip assembly of claim 20 wherein said soft body of said transitional tip portion is made of a plastic material having shore "D" durometer of approximately 55.

25. The catheter tip assembly of claim 20 wherein said elongate soft tubular body is made of a plastic material having shore "A" durometer of substantially 80 A.

26. The catheter tip assembly of claim 20 wherein said proximal end of said wire coil in said elongate soft tubular body has a length of substantially 2 cm.±5 mm.

27. The catheter tip assembly of claim 20 wherein said catheter body is made of a material having cross-braided reinforcement members therein.

28. The catheter tip assembly of claim 20 wherein said elongate soft tubular body has a length of between 10–20 cm.

29. The catheter tip assembly of claim 20 wherein said elongate soft tubular body has an outer diameter of substantially 0.066 inches.

30. The catheter tip assembly of claim 20 including a tip plug fixed to the outer end of said elongate soft tubular body.

31. The catheter tip assembly of claim 20 wherein said tip plug is made of a plastic material having a shore "D" durometer of substantially 55.

32. The catheter tip assembly of claim 20 wherein said first high stress resistant connection is further defined by said conical distal end of said catheter body having a length of substantially 1.5 cm.

33. The catheter tip assembly of claim 20 wherein said elongate soft tubular body has a length of between 12–15 cm.

34. A catheter flexible tip assembly combined with and mounted to the distal end of a catheter body, said catheter body having high torque and high kink resistant characteristics, having a central lumen and having a distal end with a conical outer surface, said tip assembly comprising an elongate soft body having a wire coil embedded therein, a distal end and a proximal end, and a high stress resistant connection between said distal end of said catheter body and said proximal end of said elongate soft body of said tip assembly, said high stress resistant connection being defined by a conical cavity in said proximal end of said elongate soft body, by said conical distal end of said catheter body being received in and heat fused to a wall of said conical cavity in said proximal end of said elongate soft body and by said wire coil in said elongate soft body having a proximal end which extends proximally beyond said proximal end of said elongate soft body and into said conical cavity and beyond the outer end of said conical cavity and is embedded in and heat fused into a wall of a distal portion of said central lumen in said catheter body.

35. A catheter flexible tip assembly combined with and mounted to the distal end of a catheter body portion, said catheter body portion having a central lumen therein, having wire reinforcement therein and having high torque and high kink resistant characteristics, said tip assembly comprising an elongate soft body having a wire coil embedded therein, a proximal end and a distal end, and a high stress resistant connection between a distal end of said catheter body portion and a proximal end of said elongate soft body, said high stress resistant connection being defined by said distal end of said catheter body portion having an enlarged bore therein with a cross-section larger than the cross-section of said central lumen, by a proximal end portion of said wire coil extending beyond the proximal end of said elongate soft body and being received in said enlarged bore and heat fused to the wall of said bore and by the distal end of said catheter body being heat butt fused to said proximal end of said elongate soft body.

36. A catheter flexible tip assembly combined with and mounted to a distal end of a catheter body, said catheter body having high torque and high kink resistant characteristics, having a central lumen and having a distal end with a conical outer surface, said tip assembly comprising an elongate soft tubular body having a wire coil embedded therein, a distal end having a proximal end, a transitional tip portion connected between said proximal end of said elongate soft tubular body and the distal end of said catheter body, a first high stress resistant connection between said distal end of said catheter body and a proximal end of said transitional tip portion defined by a conical cavity in said proximal end of said transitional tip portion, and by said conical distal end of said catheter body being received in and heat fused to a wall of said conical cavity in said proximal end of said transitional tip portion and a second high stress resistant connection between a distal end of said transitional resistant connection between a distal end of said transitional tip portion and said proximal end of said elongate soft tubular body defined by said distal end of said transitional tip portion having an enlarged bore therein with a cross-section larger than the cross-section of said central lumen, by a proximal end portion of said wire coil extending beyond said proximal end of said elongate tubular body and being received in said enlarged bore and heat fused to the wall of said bore and by the distal end of said transitional tip portion being heat butt fused to a proximal end of said elongate soft tubular body.

* * * * *

UNITED STATES PATENT AND TRADEMARK OFFICE
CERTIFICATE OF CORRECTION

PATENT NO. : 5,571,073
DATED : November 5, 1996
INVENTOR(S) : Frank O. Castillo

It is certified that error appears in the above-indentified patent and that said Letters Patent is hereby corrected as shown below:

Column 5, line 37, after "wherein" insert --said--.

Signed and Sealed this

Twenty-ninth Day of April, 1997

Attest:

BRUCE LEHMAN

*Attesting Officer*   *Commissioner of Patents and Trademarks*